United States Patent [19]
Bachinski et al.

[11] Patent Number: 5,800,525
[45] Date of Patent: Sep. 1, 1998

[54] BLOOD FILTER

[75] Inventors: Thomas J. Bachinski, Lakeville; David S. Goldsteen, Minneapolis; Daniel J. Sullivan, Medina, all of Minn.

[73] Assignee: Vascular Science, Inc., Minneapolis, Minn.

[21] Appl. No.: 868,957

[22] Filed: Jun. 4, 1997

[51] Int. Cl.⁶ .................................................. A61F 2/06
[52] U.S. Cl. .................................................. 623/1; 606/200
[58] Field of Search .................. 623/1, 12; 606/195, 606/198, 200

[56] References Cited

U.S. PATENT DOCUMENTS

| | | | |
|---|---|---|---|
| 4,494,531 | 1/1985 | Gianturco | 606/200 |
| 5,304,194 | 4/1994 | Chee | 606/198 |
| 5,344,427 | 9/1994 | Cottenceau | 606/200 |
| 5,549,626 | 8/1996 | Miller | 606/195 |
| 5,601,595 | 2/1997 | Smith | 606/200 |
| 5,618,301 | 4/1997 | Hauenstein | 623/1 |
| 5,634,942 | 6/1997 | Chevillon | 623/1 |
| 5,709,704 | 1/1998 | Nott | 606/200 |

*Primary Examiner*—Michael J. Milano
*Attorney, Agent, or Firm*—Fish & Neave; Jeffrey H. Ingerman

[57] ABSTRACT

A bodily fluid filter has an elastic tubular framework and a plurality of filter filaments extending from the surface of the tubular framework in toward the longitudinal axis to trap objects to be filtered. The elastic framework is deformable to facilitate deployment and removal, but resumes its operational shape once deployed. The filter can be installed intralumenally and/or remotely if desired.

41 Claims, 5 Drawing Sheets

BLOOD FILTER

BACKGROUND OF THE INVENTION

This invention relates to a blood filter, and more particularly to a blood filter which can be installed intralumenally. The invention also relates to methods and apparatus for delivering and installing a blood filter intralumenally.

Increasing numbers and types of intralumenal procedures are being performed on medical patients. For example, there are intravascular blood flow measurement procedures, intravascular atherectomy procedures, intravascular drug therapy procedures, balloon angioplasty procedures, intravascular stent installation procedures, and even intravascular coronary bypass procedures (see, for example, Goldsteen et al. U.S. patent application Ser. No. 08/745,618, filed Nov. 7, 1996, which is hereby incorporated by reference herein in its entirety). These procedures may result in the dislodging or formation of emboli (i.e., foreign objects, including but not limited to clots, debris or bubbles of air or other gas), that should not be allowed to flow freely through the patient's circulatory system. Therefore, it may be necessary to deploy a filter to trap such objects and then remove them, or wait until they dissolve as a result of natural body processes or under the influence of medication. Some of the locations where filters need to be deployed may be located very remotely from where the medical instrumentation enters the patient's body. Such filters may therefore be conveniently deployable only intravascularly.

The above-mentioned intravascular procedures are only some examples of where filters may be needed to be deployed in body fluid conduits. Other body fluid flow conduits—e.g., in the lymph system or the digestive system—may need to have filters deployed in them, and again it may be desired to deliver a filter to such a location intralumenally.

In view of the foregoing it would be desirable to be able to provide improved bodily fluid filters.

It is also desirable to be able to provide bodily fluid filters that can be installed intralumenally and/or remotely if desired.

It is further desirable to be able to provide methods and apparatus for installing bodily fluid filters.

It is still further desirable to be able to provide methods and apparatus for intralumenally and/or remotely installing bodily fluid filters.

It is yet further desirable to be able to provide methods for making bodily fluid filters.

SUMMARY OF THE INVENTION

It is an object of this invention to provide improved bodily fluid filters.

It is also an object of this invention to provide bodily fluid filters that can be installed intralumenally and/or remotely if desired.

It is a further an object of this invention to provide methods and apparatus for installing bodily fluid filters.

It is a still further an object of this invention to provide methods and apparatus for intralumenally and/or remotely installing bodily fluid filters.

It is yet a further an object of this invention to provide methods for making bodily fluid filters.

In accordance with this invention there is provided a bodily fluid filter including a tubular framework of a first elastic material having a longitudinal axis, and forming a tubular bodily fluid flow passageway having a tubular wall, and a plurality of filaments extending from the tubular framework into the tubular bodily fluid flow passageway for trapping solid objects flowing in the bodily fluid flow passageway without obstructing the bodily fluid flow.

A method of making such a filter, as well as a method and apparatus for deploying such a filter, are also provided.

BRIEF DESCRIPTION OF THE DRAWINGS

The above and other objects and advantages of the invention will be apparent from the following detailed description, taken in conjunction with the accompanying drawings, in which like reference characters refer to like parts throughout, and in which.

DETAILED DESCRIPTION OF THE INVENTION

Figure 1:
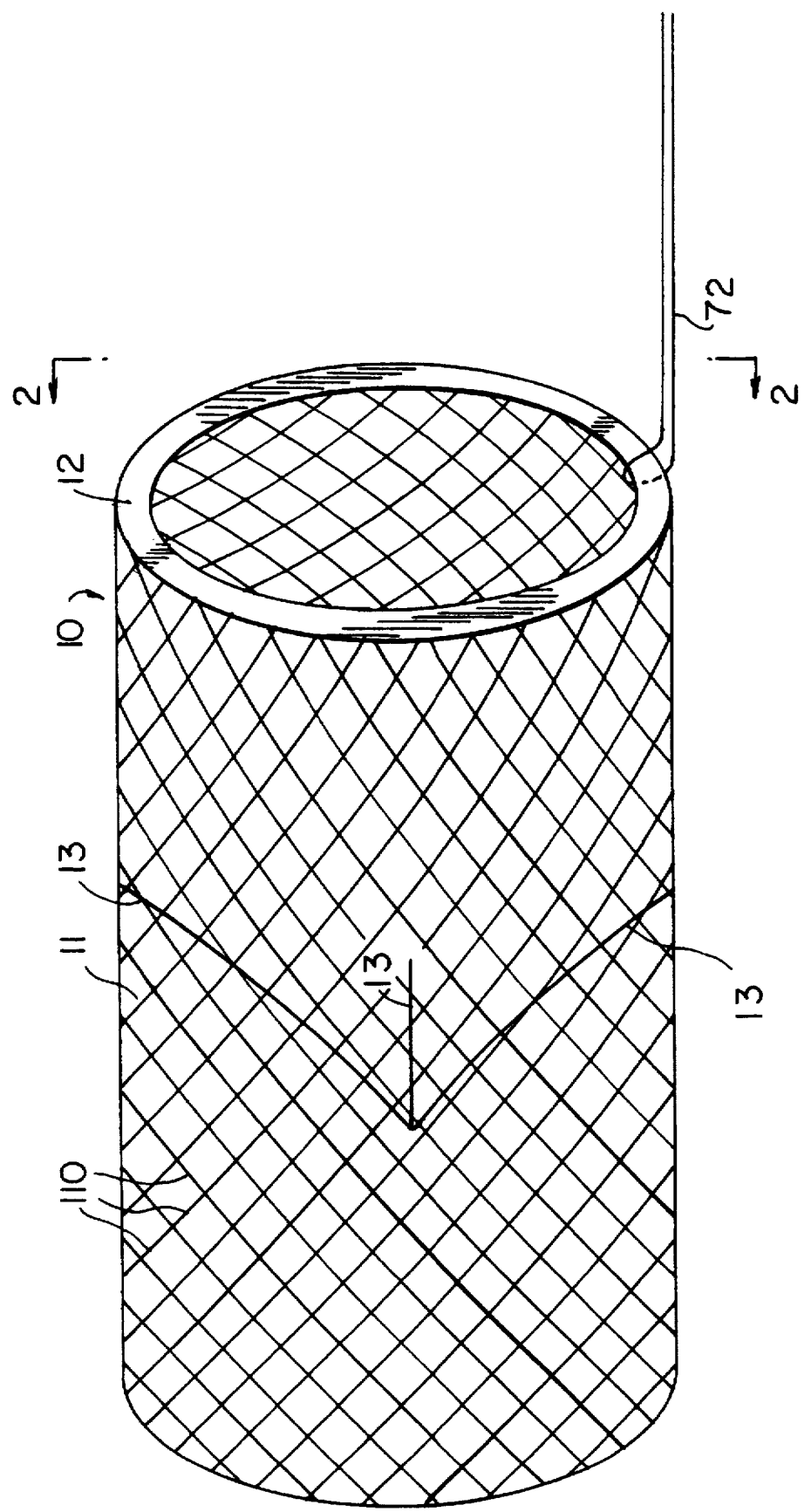
FIG. 1 is a perspective view of a preferred embodiment of a blood filter according to this invention.
Figure 2:
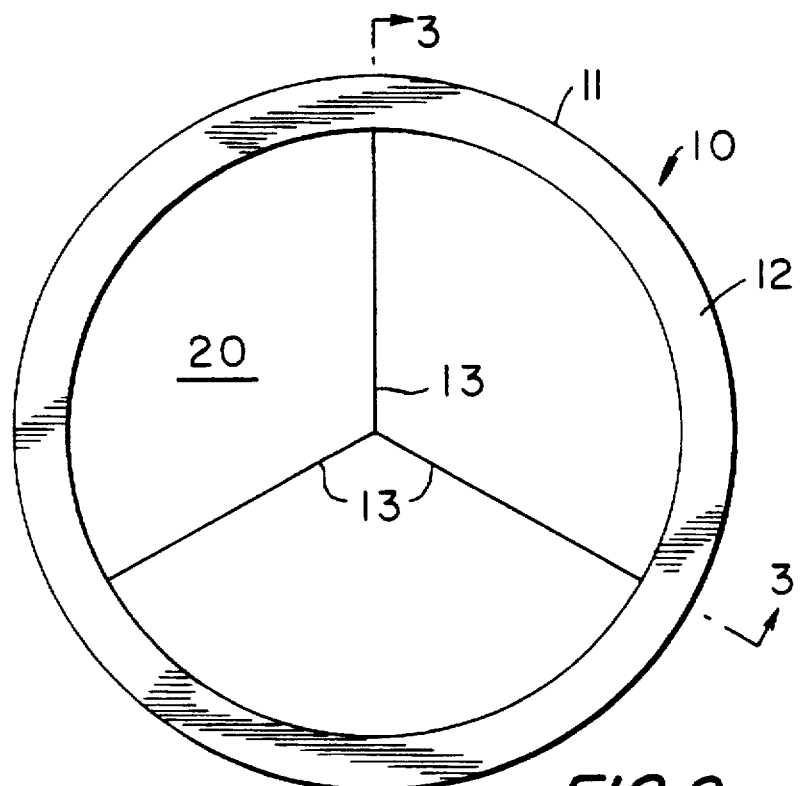
FIG. 2 is an end elevational view of the blood filter of FIG. 1, taken from line 2—2 of FIG. 1.
Figure 3:
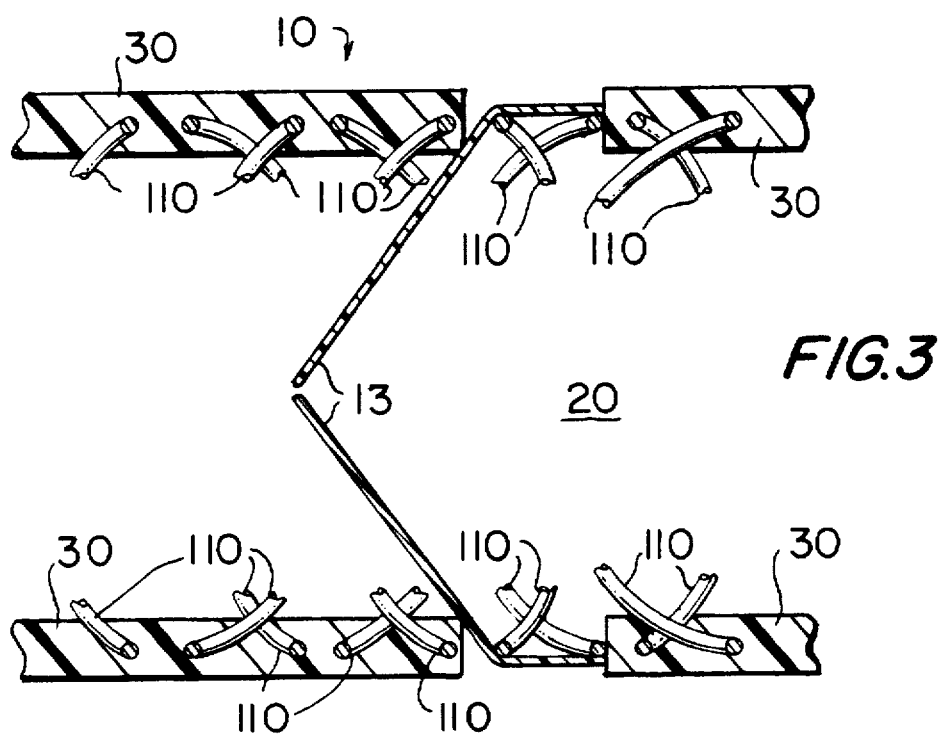
FIG. 3 is a fragmentary cross-sectional view of the blood filter of FIGS. 1 and 2, taken from line 3—3 of FIG. 2, showing a first preferred attachment of the filtering filaments to the tubular framework.

The present invention provides a blood filter, or a filter for other bodily fluids, that can be deployed in a bodily fluid conduit, such as a blood vessel, either permanently or temporarily. The bodily fluid filter will trap solid debris in the bodily fluid, and prevent it from damaging organs or other body structures downstream. For example, if deployed in a blood vessel during an intravascular procedure, the bodily fluid filter according to the invention may trap emboli that form during the procedure. Eventually, natural body processes preferably will dissolve the emboli, so that the bodily fluid filter, and therefore the blood vessel, does not become occluded. In the case of a temporary deployment, however, dissolution of the obstructions is not so important, because the bodily fluid filter can and will be removed if, or before, it becomes clogged. To that end, the bodily fluid filter according to the invention preferably is provided with a structure, such as a trailing loop, by which it can be removed. In certain circumstances, depending on the nature of the objects to be filtered from the bodily fluid, it may be possible to leave the bodily fluid filter in place more or less permanently, knowing that it will never become permanently clogged, but will filter dissoluble objects that might cause damage if allowed to flow unimpeded. For example, a patient with a blood-clotting disorder such as phlebitis might have a bodily fluid filter according to the invention inserted semi-permanently—e.g., in the carotid artery to keep clots out of the brain—in conjunction with some kind of drug therapy to dissolve clots. The trailing loop is therefore preferably removable after deployment of the bodily fluid filter, if desired.

A preferred embodiment of a bodily fluid filter, such as a blood filter (hereafter, the term "blood filter" will be used, but is should be understood that other types of bodily fluid filters are within the contemplated scope of this invention) according to this invention includes a tubular framework of a first highly elastic material. For example, this framework may be a mesh made of a nickel-tin alloy commonly referred to as nitinol. A particularly preferred structure for the framework is a mesh, especially a braid, of nitinol wires. However, other metals, as well as polymeric materials, may also be used. Moreover, while the framework of the plug is preferably a braided wire structure, it can be formed in any of many different ways. For example, apertures could be cut in an initially imperforate structure. Alternatively, a mesh of strands of the framework material could be formed by a method other than braiding, such as knitting, weaving, or felting together strands of framework material, etc.

For some applications, particularly where the blood filter is to be left in place, the framework may covered with a preferably substantially continuous web of a second highly elastic, rubber-like material. The covering may be inside the framework, outside the framework, or both inside and outside the framework. The framework is preferably at least partly embedded in the covering. Preferred rubber-like materials for the covering preferably are bio-compatible and preferably are polymeric materials, especially polymeric rubber materials. A particularly preferred rubber-like material is silicone. Examples of other suitable rubber-like materials are stretchable urethane, stretchable polytetrafluoroethylene (PTFE; also known by the trademark TEFLON® owned by E. I. du Pont de Nemours and Company), natural rubber, and the like. For some applications it may be desirable to make the covering porous. Other applications may not benefit from such porosity. Thus the covering can be either porous or non-porous as desired. Illustrative porosities and techniques for producing porosity are described in the above-incorporated application Ser. No. 08/745,618, in the context of artificial graft structures which can have coverings similar to the coverings used on the blood filter of this invention.

The blood filter may include one or more coatings over the covering. The coating(s) may be inside the tubular passageway, outside the tubular passageway, or both inside and outside the tubular passageway. Possible coating materials include bio-compatible materials and/or drugs. Examples include hydrophilic polymers such as hydrophilic polyurethane (to create a lubricious surface), parylene (a polymer commonly used to coat pacemakers), PTFE (which may be deposited from a PTFE vapor using a process that is sometimes called vapor transport), the drug Heparin (a common anti-coagulant), collagen, human cell seeding, etc. One purpose of such a coating, which is more likely to be used when the blood filter is to remain in place more or less permanently, may be to give the coated surface a very high degree of bio-compatibility and/or a very high degree of smoothness. Any coatings that are used preferably do not interfere with the elasticity of the blood filter. The coating(s) may be applied at any suitable and convenient time during the manufacture of the blood filter. The coating(s) may be applied using any suitable technique such as dipping, electrostatic spraying, vapor transport, in vitro cell reproduction, etc.

The filtering function of a blood filter according to this invention preferably is provided by a plurality of filaments affixed to the tubular framework and extending into the tubular passageway formed by the framework. Preferably, the filaments meet substantially at a point substantially along the longitudinal axis of the tubular framework. The point at which the filaments meet is preferably longitudinally displaced from one or more of the points along the framework at which the filaments are attached, so that the filaments form a substantially cone-shaped basket. Most preferably, all of the filaments are attached along a circle extending circumferentially about the longitudinal axis, so that the filter basket is substantially a right-circular cone. The filaments may be affixed to one another at the point at which they meet, but preferably they are not. However, the filaments preferably are stiff enough to trap emboli or other objects even if the filaments are not affixed to one another.

Preferably, the filter filaments are made of the same material as the tubular framework. Thus, in the preferred embodiment in which the framework is a braided nitinol mesh, the filaments preferably are nitinol wires. The wires preferably are affixed to the mesh, as by welding, and particularly YAG laser welding, and preferably are not affixed to one another where they meet. However, if they are affixed to one another, they preferably are affixed, again, by welding.

The filaments are preferably equiangularly spaced around the longitudinal axis of the tubular framework. That way, no one space between filaments will allow the passage of an object larger than could pass through any other such space. The number of filaments depends on the radius of the tubular framework and the expected size of the objects to be filtered. In particular, for n filaments, the blood filter according to the invention will allow the passage of an object having a diameter on the order of $2r\sin(\pi/n)$, which is the length of a line segment connecting the ends of two adjacent ones of n equiangularly spaced filaments at the surface of a tubular framework of radius r. For the intravascular coronary bypass procedure described in said above-incorporated application Ser. No. 08/745,618, the preferred number n of filaments is three, based on the radii of the coronary arteries and the size of the expected emboli. However, for larger body fluid conduits or smaller expected objects to be filtered, a greater number n of filaments may be provided.

In an alternative arrangement, the filaments may extend substantially parallel to one another between points on the surface of the tubular framework. In such an arrangement, the number n of filaments preferably is selected so that the spacing between filaments—i.e., $2r/n$ in a tube of radius r—is substantially no larger than about the size of the expected object to be filtered. In this arrangement, each filament may be affixed to the tubular framework at both ends of the filament, or at only one end of the filament.

For reasons that will be apparent below in connection with a description of a method of deploying a blood filter according to the present invention, it is preferable that the filaments in the embodiment in which the filaments meet at a point not be connected to one another, and that the filaments in the embodiment in which the filaments are parallel not be connected to the framework at both ends. Moreover, it is more particularly preferred, if the framework is an extendable mesh, that when the mesh is extended the filaments assume a position substantially lying along the walls of the framework, as discussed below.

The filaments are preferably affixed directly to the structure of the tubular framework, as by welding. Thus, if the framework is a braided mesh of strands, each filament can be welded to a strand. Alternatively, in the case of a braided mesh, a base filament can be threaded through the mesh circumferentially, through the interstices of the mesh, and the filaments can be affixed, again as by welding, to the base filament. Of course, the filaments can be attached other than by welding, either to the framework itself or to the base filament.

If the tubular framework is a braided mesh of elastic material as is preferred, then it will be longitudinally extendable, and, preferably, when it is extended longitudinally its diameter will decrease. It is for this reason that, as discussed above, it is preferred that when the framework is extended, the filaments assume a position substantially along the wall of the tubular framework. A particularly preferred way of accomplishing this result is to guide each filament from its attachment point along the exterior of the tubular framework past at least one strand of the braid and then in through an interstice between strands in the tube wall, before bending it to extend toward the tube axis. It can readily be visualized that when the braided framework is extended, the filament will be pulled partially out through the interstice, which will cause it to tend to lie along the tube wall. When the tube is relaxed, the filament will return to its operational position.

An preferred technique for making a blood filter according to the invention is to braid nitinol wire having a gauge of between about 0.002 inch and about 0.003 inch on a 0.350 inch diameter rod. (The dimensions given herein are only illustrative and will vary depending on the desired size of the blood filter) The wire mesh is then treated (e.g., with heat) to cause it to set in the shape that it has on the forming rod. The forming rod is then removed. The filter filaments are then preferably welded in place and threaded through the mesh as described above. The blood filter may then be heated again to set the filter filaments. The resulting framework preferably is coated with silicone to produce a substantially continuous web on the framework, preferably without coating the filter filaments.

A preferred method of installing a blood filter in accordance with this invention includes deforming the blood filter so that its diameter decreases, guiding the deformed blood filter into place through the patient's vascular system to the installation location, and then allowing the blood filter to resume its original diameter. Using the preferred braided mesh embodiment, the deformation necessary to achieve the required reduction in diameter preferably would be elongation of the blood filter.

Apparatus for installing a blood filter in accordance with the above-described method may include a device by which the blood filter can be elongated. For example, a tubular mandrel around which the blood filter can be placed and elongated could be used. It is for this reason that it is preferred that the filter wires not be bonded where they meet, so that they can move out of the way and allow the insertion of the mandrel in the tubular passageway of the blood filter. However, in an embodiment in which the wires are bonded where they meet, other apparatus for elongating the blood filter, such as a device that grasps both ends of the blood filter and stretches it, and then holds it in the stretched position as it is guided through the vascular system, can be used.

A releasable retainer mechanism is used to releasably hold the blood filter on the mandrel in the preferred embodiment. The releasable retainer preferably is a wire that is looped through at least one interstice of the braided structure and doubled over, and then allowed to trail out of the patient. By maintaining tension on the wire, one can maintain the blood filter in its elongated form so that it hugs the surface of the mandrel. To release the blood filter from the mandrel, one can release the tension on the wire. The blood filter will expand against the wall of the blood vessel, and the mandrel can be removed. If the blood filter is to remain permanently, the retainer wire can be pulled out by pulling on only one of the doubled over strands. If the blood filter is to be removed later, the wire is left in place. When it is time to remove the blood filter, the mandrel can be reinserted through the vascular system, tension can be put on the wire to lengthen and narrow the blood filter so that it again hugs the mandrel, and the mandrel can then be removed, with tension maintained on the wire to retain the blood filter on the mandrel during removal. To facilitate insertion and removal of the mandrel with the blood filter in place thereon, an outer tube surrounding and spaced away from the mandrel can be provided. If such a tube is used, the trailing removable retainer wire is normally (but not necessarily) threaded through the outer tube.

The invention will now be described with reference to FIGS. 1–7.

FIGS. 1–4 show a first preferred embodiment of a blood filter 10 according to the present invention. Blood filter 10 preferably has a tubular framework 11 which preferably is a mesh structure of preferably highly elastic fibers, which preferably are nitinol wires 110 as discussed above. While the mesh preferably is braided, it may also be knitted, woven, felted, etc. as discussed above.

Tubular framework 11 preferably has an end structure 12, which preferably facilitates the operation of the retention/withdrawal loop, as discussed above and as shown below, by providing a reinforced structure on which the retention/withdrawal loop may act. End structure 12 may include additional nitinol wires, similar to wires 110, woven circumferentially through the ends of framework 11, or it may include a heavier strand of nitinol or other elastic or even inelastic material.

The filtering function of blood filter 10 preferably is performed by filter filaments 13 which are affixed to tubular framework 11. Filaments 13 extend inwardly from tubular framework 11 into tubular fluid flow space 20, through which blood or other bodily fluid flows when blood filter 10 is deployed. In a particularly preferred embodiment shown in FIG. 2, filaments 13 meet substantially at the longitudinal axis of blood filter 10. However, it is not necessary that they meet at the axis; they could meet elsewhere. Indeed, they need not meet at all; in an alternative embodiment shown in FIG. 6, filaments 513 extend across fluid flow space 20 substantially parallel to one another, as discussed in more detail below.

In an embodiment in which filaments 13 do meet, as shown in FIGS. 1–4, the points at which the filaments 13 are attached to tubular framework 11 and the point at which filaments 13 meet could all be at different positions as measured along the direction of the longitudinal axis of blood filter 10, so that the "filter basket" formed by filaments 13 has a generalized conical shape. Preferably, and as shown in FIGS. 1–4, the points of attachment of all of filaments 13 are at the same axial position, with the point at which filaments 13 meet axially offset from that position, so that the filter basket is substantially a right circular cone. Alternatively (not shown), even the point at which filaments 13 meet could be at the same axial position as the attachment points, so that the "basket" is a planar screen perpendicular to the longitudinal axis of blood filter 10. In still another alternative (not shown), the attachment points and the meeting point could again all be in a plane, but that plane could be inclined at an angle other than 90° relative to the longitudinal axis.

The number of filaments 13 depends on the diameter of tubular framework 11, which in turn is a function of the diameter of the blood vessel or other tubular body organ into which blood filter 10 is to be deployed, as well as on the expected size of the emboli or other debris to be trapped. The filter basket should not be able to pass any object larger than a specified size. For example, in the embodiment shown in FIG. 2, where filaments 13 are arranged radially and meet at the longitudinal axis, the filter basket would trap objects having a diameter larger than about $2r\sin(\pi/n)$, where r is the radius of tubular framework 11 and n is the number of filaments, which is the distance from the end of one filament 13 to the end of an adjacent filament 13. Generally, the larger the diameter of blood filter 10, the more filaments 13 there normally would be (i.e., the more n would be increased) to avoid allowing objects to escape filtration.

Each filament 13 preferably is fastened at one end to tubular framework 11, as by welding or other suitable bonding technique. At the other end, where each filament 13 (preferably) meets the other filaments 13, the filaments 13 may be bonded to one another. However, they preferably are not bonded at that point, so that they can assume a position along or closer to the wall of tubular framework 11 when necessary. If filaments 13 are not bonded to one another, they may need to be stiffer than if they are bonded to one another, if they are to have the same ability to trap large objects without being pushed aside.

Figure 4:
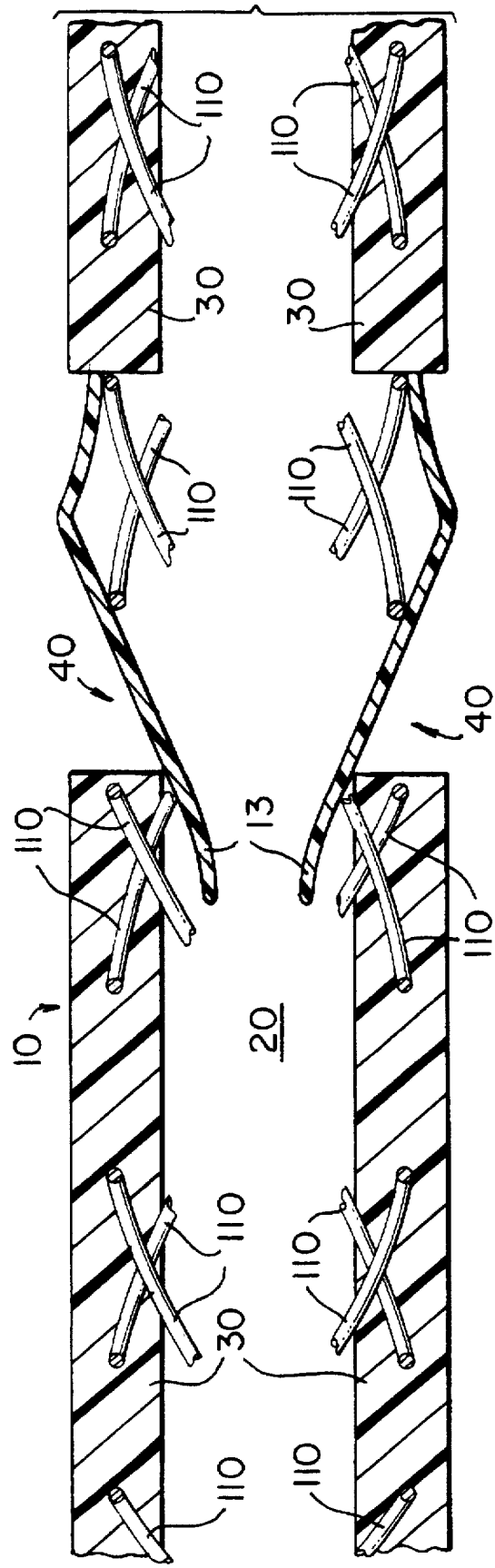
FIG. 4 is a fragmentary cross-sectional view of the blood filter of FIGS. 1–3 in a longitudinally extended condition.

Having filaments 13 assume a position along or closer to the wall of tubular framework 11 may be necessary during deployment of blood filter 10, which preferably is carried out using a mandrel that is inserted intravascularly, and on which blood filter 10 rides. The preferably braided nature of elastic tubular framework 11 is preferably such that as tubular framework 11 is elongated, its diameter decreases. In addition, the individual fibers or wires that make up tubular framework 11 move further away from one another, so that the interstices between them also move apart. If a filament 13 is passed from its point of attachment on tubular framework 11 along the outside of tubular framework 11 past at least one additional wire, and then inward toward the longitudinal axis through an interstice in tubular framework 11, then as the interstices move away from one another, filament 13 will be pulled partially out of the interstice through which it enters, as shown in FIG. 4, to assume a position along or closer to the wall of tubular framework 11. As tubular framework 11 is relaxed, filaments 13 will resume their "upright" positions. Other techniques for causing filaments 13 to assume a position along or closer to the wall of tubular framework 11 can also be used.

As discussed above, tubular framework 11 can be coated with a web 30 of suitable elastic material such as silicone or the other alternatives discussed above. The material should be able to expand at least as far as the elastic fibers 111. Such a web 30 is most likely to be provided in cases where blood filter 10 is to be left more or less permanently in the patient. If a web 30 is provided in an embodiment such as that just described where filaments 13 pass through interstices in tubular framework 11 for the purpose of causing them to lie down or stand up as tubular framework 11 is stretched or relaxed, then it may be preferable to provide gaps 40 in web 30 where filaments 13 pass through web 30, to prevent interference with the movement of filaments 13.

Figure 5:
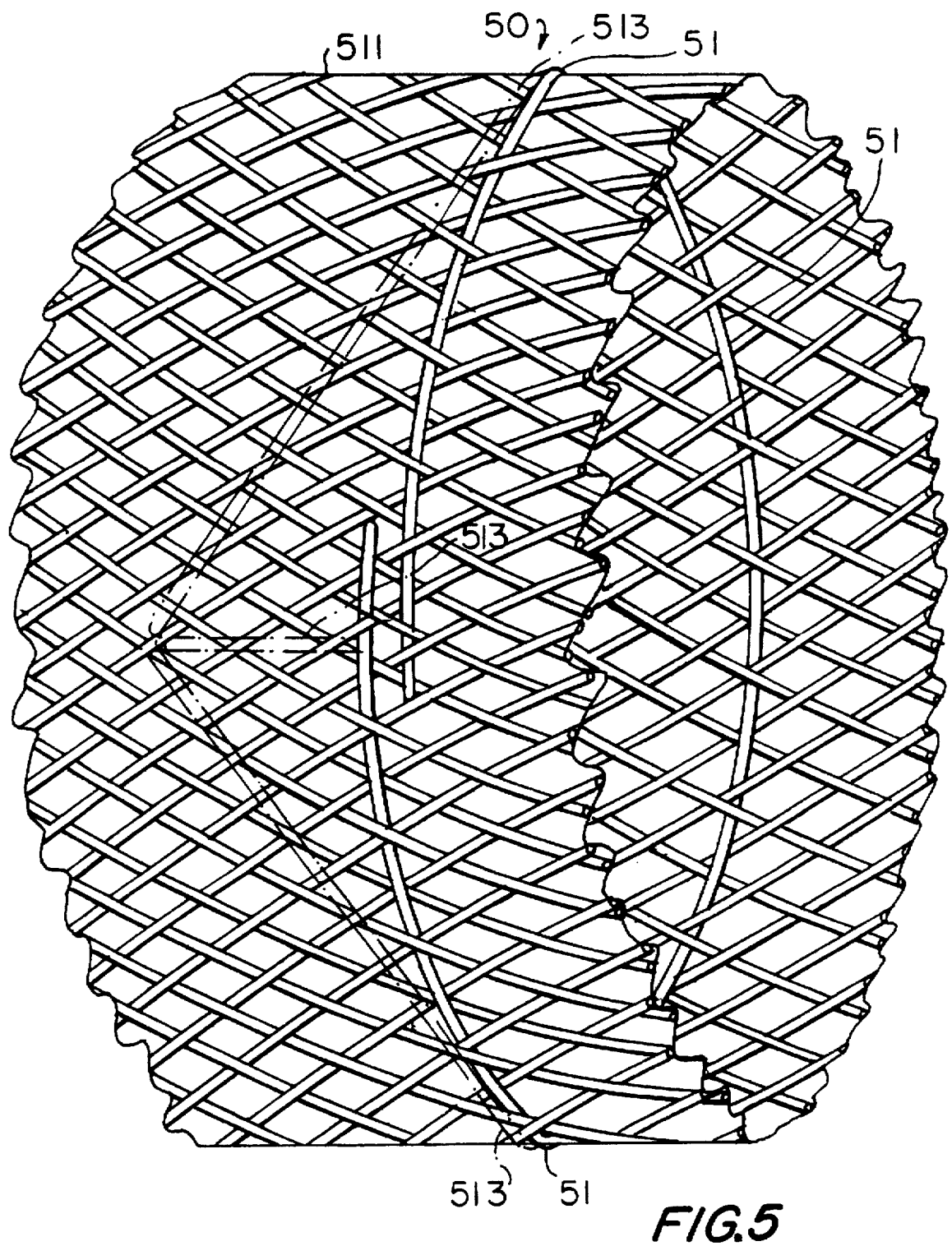
FIG. 5 is a fragmentary cross-sectional view of the blood filter of FIGS. 1 and 2, showing a second preferred attachment of the filtering filaments to the tubular framework.

In a variant of the preferred embodiment of a blood filter 50 according to the invention, shown in FIG. 5, instead of welding filter filaments 513 to tubular framework 511, a base filament 51 could be threaded through tubular framework 511 circumferentially (or with any desired orientation), and filaments 513 could be welded or otherwise fastened to base filament 51. Base filament 51 preferably is not fastened other than by threading to tubular framework 511 so that as the diameter of tubular framework 511 varies, such as during deployment, base filter 51 does not interfere with those variations.

Figure 6:
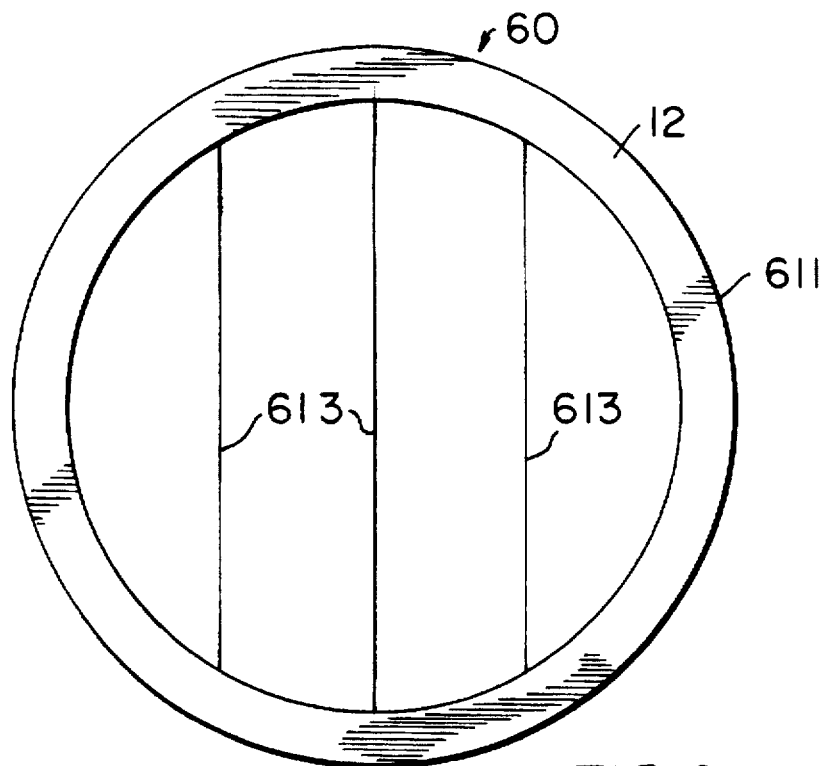
FIG. 6 is an end elevational view, similar to FIG. 2, of a second preferred embodiment of a blood filter according to the invention.

In another preferred embodiment 60, shown in FIG. 6, each filter filament 613 extends from one point on tubular framework 611 to another point on tubular framework 611. In the particularly preferred variant of this embodiment shown in FIG. 6, filaments 613 are substantially parallel to one another. Once again, the number n of filaments 613 will likely increase with the diameter of blood filter 60, and the spacing between filaments 613, which is preferably substantially uniform at $2r/n$, where r and n have the same meanings as above, is chosen based on the size of the expected objects to be filtered. As in the prior embodiment, each filament 613 could be attached to tubular framework 611 at both ends, but preferably is attached only at one end so that it can move out of the way, and it preferably is arranged so that it moves out of the way as blood filter 60 is extended. Of course, if filaments 613 are sufficiently elastic, they be able to be stretched sufficiently to be pushed aside even if they are attached at both ends to tubular framework 611, but the resulting tension in filaments 613 may make it difficult to easily remove any structure inserted therethrough, which would limit the usefulness of inserting any such structure.

Figure 7:
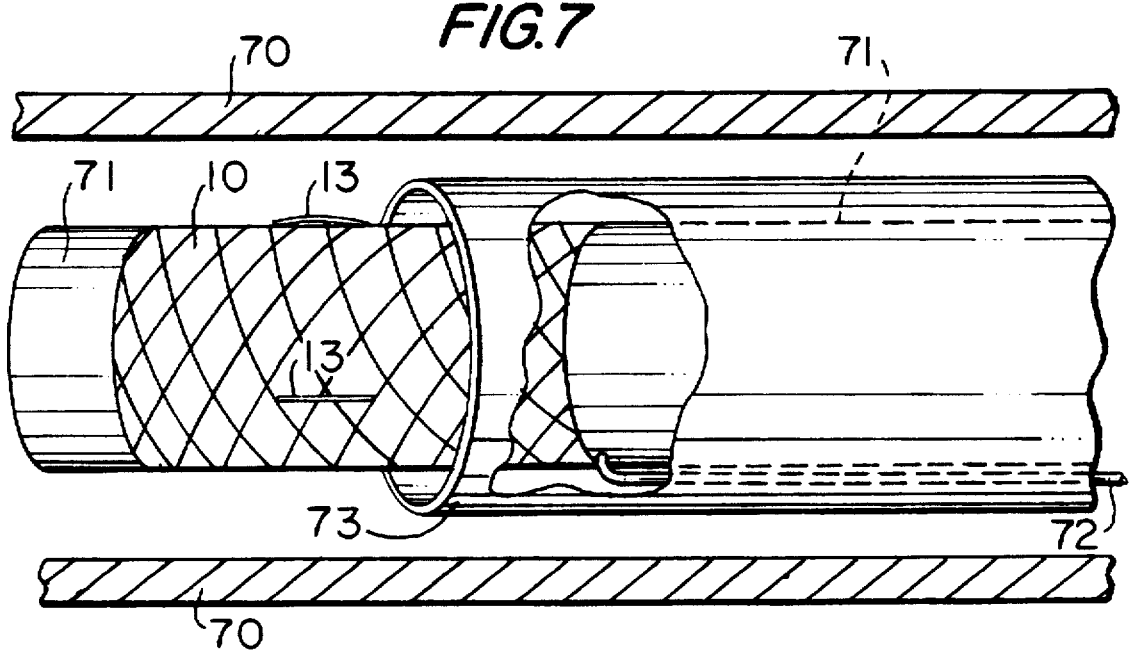
FIG. 7 is a simplified perspective view of a preferred embodiment of apparatus for installing the blood filters of FIGS. 1–6.

As shown in FIG. 7, blood filter 10 (or 50 or 60) according to this invention preferably is inserted in blood vessel (or other tubular body organ) 70 on a mandrel 71, which is inserted into vessel 70 through an incision (not shown) remote from the deployment site. As can be seen, filaments 13 are folded along the wall of tubular framework 11 to allow mandrel 71 to pass through blood filter 10. If filaments 13, 513, 613 were fixed at both ends, they could not fold along the wall, and mandrel 71 could only be inserted part of the way into blood filter 10 (or 50 or 60), making mandrel 71 an unsuitable insertion device. In such a case, a more complex device (not shown), such as one that grabs both ends of blood filter 10, 50, 60 from the outside and pulls the ends apart to decrease the diameter, would have to be used.

To retain blood filter 10, 50, 60 on mandrel 71, a retainer member is provided, which preferably is a wire loop 72, preferably passing around end structure 12, or through one or more interstices if there is no end structure 12. The ends of wire loop 72 trail behind as mandrel 71 is inserted and maneuvered into place, preferably extending out of the patient, where they tension can be maintained on them to keep blood filter 10, 50, 60 extended and therefore of a diameter small enough to retain it on mandrel 71. When blood filter 10, 50, 60 reaches the deployment position, the tension on loop 72 can be released, allowing the diameter of blood filter 10, 50, 60 to expand to its normal size, which is selected so that blood filter 10, 50, 60 fits snugly against the walls of blood vessel 70. If blood filter 10, 50, 60 is to be left in place in the patient, then after deployment one end only of loop 72 can be pulled, extracting loop 72 from the patient. If blood filter 10, 50, 60 is to be removed, then after deployment loop 72 is left in place, trailing out of the incision in the patient (not shown). Mandrel 71 is removed, and whatever procedure is to be carried out is carried out. Mandrel 71 is then reinserted until it reaches the location of blood filter 10, 50, 60, and tension is applied to loop 72 so that blood filter 10, 50, 60 contracts onto the surface of mandrel 71. Then tension on loop 72 is maintained until blood filter 10, 50, 60 is extracted from the patient, to keep blood filter 10, 50, 60 on mandrel 71 during extraction.

An optional delivery tube 73 can be placed around mandrel 71, with blood filter 10, 50, 60 inserted between mandrel 71 and tube 73, so that a smoother surface is presented to the walls of vessel 70 as mandrel 71 is guided to the deployment position. Mandrel 71 would have to be extended out of tube 73, or tube 73 would have to be retracted, for deployment to occur. If tube 73 is used, the trailing ends of loop 72 would preferably run inside tube 73.

Tube 73 could even be used without mandrel 71, as long as some structure for pushing blood filter 10, 50, 60 out of tube 73 could be provided. In such a case, tension would be applied to blood filter 10, 50, 60 so that it contracts, allowing it to be placed in tube 73, with loop 72 trailing. Tension would then be released so that blood filter 10, 50, 60 expands against the walls of tube 73. Tube 73 would be guided into position and tension would be applied via loop 72 so that blood filter 10, 50, 60 again contracts, allowing it to be expelled from tube 73 by an appropriate structure. Tension would again be released so that blood filter 10, 50, 60 expands against the walls of vessel 70. To remove blood filter 10, 50, 60, tension would be applied via loop 72 to cause blood filter 10, 50, 60 to contract so that it fits inside tube 73. Tension would be released so that blood filter 10, 50, 60 expands against the walls of tube 73. Tube 73 would be withdrawn from the patient and tension would be applied via loop 72 so that blood filter 10, 50, 60 again contracts, allowing it to be removed from tube 73.

Thus it is seen that improved bodily fluid filters, that can be installed intralumenally and/or remotely if desired, as well as methods and apparatus for installing bodily fluid filters and for intralumenally and/or remotely installing bodily fluid filters, as well as methods for making bodily fluid filters, have been provided. One skilled in the art will appreciate that the present invention can be practiced by other than the described embodiments, which are presented for purposes of illustration and not of limitation, and the present invention is limited only by the claims which follow.

What is claimed is:

1. A bodily fluid filter comprising:
    a tubular framework of a first elastic material having a longitudinal axis, and forming a tubular bodily fluid flow passageway having a tubular wall; and
    a plurality of filaments extending from said tubular framework into said tubular blood flow passageway for trapping solid objects flowing in said bodily fluid flow passageway without obstructing said bodily fluid flow.

2. The bodily fluid filter of claim 1 wherein at least one of said filaments extends from a proximal end thereof at a first point on said tubular framework across a portion of said tubular passageway to a distal end thereof at a second point on said tubular framework.

3. The bodily fluid filter of claim 2 wherein said plurality of filaments extend substantially parallel to one another.

4. The bodily fluid filter of claim 1 wherein at least one of said filaments extends from a proximal end at a first point on said tubular framework substantially toward said longitudinal axis.

5. The bodily fluid filter of claim 4 wherein each of said filaments extends from a respective proximal end at a respective first point on said tubular framework substantially toward said longitudinal axis.

6. The bodily fluid filter of claim 5 wherein respective distal ends of said filaments meet at a common second point substantially along said longitudinal axis.

7. The bodily fluid filter of claim 6 wherein said distal ends of said filaments are affixed to one another at said second point.

8. The bodily fluid filter of claim 6 wherein said second point is displaced from each of said respective first points in a direction along said longitudinal axis, whereby said filaments form a cone-shaped basket.

9. The bodily fluid filter of claim 1 wherein said framework comprises a mesh of said first elastic material.

10. The bodily fluid filter of claim 9 wherein said framework comprises a braid of strands of said first elastic material.

11. The bodily fluid filter of claim 9 wherein said filaments comprise said first elastic material.

12. The bodily fluid filter of claim 9 wherein said proximal end of each of said filaments is welded to at least a respective one of said strands.

13. The bodily fluid filter of claim 12 wherein at least one of said filaments passes outside said mesh framework and into said tubular passageway through an interstice in said mesh framework; whereby:
    when said tubular mesh framework is extended longitudinally, said at least one of said filaments assumes a position lying substantially parallel to, and substantially adjacent to, said wall.

14. The bodily fluid filter of claim 10 further comprising:
    a base filament extending circumferentially at least once around said tubular wall; wherein:
    said proximal end of each of said filaments is welded to said base filament.

15. The bodily fluid filter of claim 14 wherein at least one of said filaments passes outside said mesh framework and into said tubular passageway through an interstice in said mesh framework; whereby:
    when said tubular mesh framework is extended longitudinally, said at least one of said filaments assumes a position lying substantially parallel to, and substantially adjacent to, said wall.

16. The bodily fluid filter of claim 14 wherein said base filament comprises said first elastic material.

17. The bodily fluid filter of claim 1 wherein said first elastic material comprises nitinol.

18. The bodily fluid filter of claim 1 further comprising a web of a second elastic material on said tubular framework.

19. The bodily fluid filter of claim 18 wherein said second elastic material includes silicone.

20. A method of making a bodily fluid filter comprising:
    forming a tubular framework of a first elastic material;
    affixing a proximal end of each of a plurality of filaments to said tubular framework extending into said tubular blood flow passageway for trapping solid objects flowing in said bodily fluid flow passageway without obstructing said bodily fluid flow;
    setting said framework; and
    covering said framework with a web of a second elastic material.

21. The method of claim 20 wherein said affixing comprises welding.

22. The method of claim 21 wherein said welding comprises YAG laser welding.

23. The method of claim 20 wherein said affixing comprises:
    extending a base filament circumferentially at least once around said tubular wall; and
    attaching said proximal end of each of said filaments to said base filament.

24. The method of claim 23 wherein said attaching comprises welding.

25. The method of claim 24 wherein said welding comprises YAG laser welding.

26. The method of claim 20 wherein said setting comprises heating said framework.

27. The method of claim 20 wherein said forming comprises braiding strands of said first elastic material.

28. The method of claim 20 wherein said first elastic material comprises nitinol.

29. The method of claim 20 wherein said second elastic material comprises silicone.

30. A method of installing a bodily fluid filter in a tubular body conduit through which a bodily fluid flows, said bodily fluid filter having a tubular framework of a first elastic material having a first diameter and a longitudinal axis, and forming a tubular bodily fluid flow passageway having a tubular wall, and a plurality of filaments extending from said tubular framework into said tubular blood flow passageway for trapping solid objects flowing in said bodily fluid flow passageway without obstructing said bodily fluid flow, said method comprising:

elastically deforming said bodily fluid filter into an elongated tube of a second diameter smaller than said first diameter;

inserting said elongated tube axially into position in said tubular body conduit; and releasing said bodily fluid filter from said elastic deforming.

31. The method of claim 30 wherein said bodily fluid filter is delivered to said position by passing said bodily fluid filter along the lumen of said conduit while said bodily fluid filter is deformed into said elongated tube.

32. The method of claim 30 wherein said elastically deforming comprises disposing said bodily fluid filter over a substantially cylindrical surface so that said bodily fluid filter deforms into said elongated tube concentrically with said substantially cylindrical surface.

33. The method of claim 32 wherein said elastically deforming further comprises releasably retaining said bodily fluid filter on said substantially cylindrical surface.

34. The method of claim 33 wherein said releasing comprises undoing said releasably retaining in order to allow said plug to move axially off said substantially cylindrical surface.

35. Apparatus for installing a bodily fluid filter in a tubular body conduit through which a bodily fluid flows, said bodily fluid filter having a tubular framework of a first elastic material having a first diameter and a longitudinal axis, and forming a tubular bodily fluid flow passageway having a tubular wall, and a plurality of filaments extending from said tubular framework into said tubular blood flow passageway for trapping solid objects flowing in said bodily fluid flow passageway without obstructing said bodily fluid flow, said apparatus comprising:

a substantially cylindrical surface over which said bodily fluid filter can be elastically deformed into an elongated tube, said elongated tube having a second diameter smaller than said first diameter and being substantially concentric with said surface; and a releasable retainer for releasably retaining said bodily fluid filter on said surface.

36. The apparatus of claim 35 wherein said releasable retainer comprises a longitudinal member forming a loop which engages said bodily fluid filter.

37. The apparatus of claim 36 wherein said loop is axially extendable relative to said surface to release said bodily fluid filter from said surface.

38. The apparatus of claim 37 wherein said loop is axially retractable relative to said surface to pull said bodily fluid filter back onto said surface.

39. The apparatus of claim 36 wherein an end of said longitudinal member is releasable so that said longitudinal member can be pulled from another end completely out of engagement with said bodily fluid filter.

40. The apparatus of claim 35 further comprising:

a tubular member disposed substantially concentrically around said bodily fluid filter on said substantially cylindrical surface, said substantially cylindrical surface and said bodily fluid filter being movable axially along said tubular member.

41. Apparatus for installing a bodily fluid filter in a tubular body conduit through which a bodily fluid flows, said bodily fluid filter having a tubular framework of a first elastic material having a first diameter and a longitudinal axis, and forming a tubular bodily fluid flow passageway having a tubular wall, and a plurality of filaments extending from said tubular framework into said tubular blood flow passageway for trapping solid objects flowing in said bodily fluid flow passageway without obstructing said bodily fluid flow, said apparatus comprising:

a tube in which said bodily fluid filter can be inserted, said tube having an inner surface and a second diameter smaller than said first diameter, such that said bodily fluid filter expands against said inner surface to retain said bodily fluid filter in said tube; and a releasable retainer for releasing said bodily fluid filter from engagement with said inner surface.

* * * * *